United States Patent

Zölss et al.

[11] 4,034,009
[45] July 5, 1977

[54] 4-UREIDO-2-ACYL PHENOXYPROPANOLAMINE

[75] Inventors: Gerhard Zölss, Linz; Heribert Pittner, Gmund; Heimo Stormann-Menninger-Lerchenthal, Linz, all of Austria

[73] Assignee: Chemie Linz Aktiengesellschaft, Austria

[22] Filed: Dec. 17, 1974

[21] Appl. No.: 533,688

[30] Foreign Application Priority Data

Dec. 20, 1973 Austria .................... 10666/73

[52] U.S. Cl. .............. 260/553 A; 260/244 R; 260/250 A; 260/256.4 H; 260/293.77; 260/326.4; 260/465 D; 260/501.17; 260/553 C; 424/250; 424/251; 424/267; 424/274; 424/304; 424/316; 424/322; 424/248.54; 424/230

[51] Int. Cl.² .............. C07C 127/15; C07C 127/19; A61K 31/17

[58] Field of Search ............... 260/553 A, 553 C

[56] References Cited

UNITED STATES PATENTS

| | | |
|---|---|---|
| 3,644,520 | 2/1972 | Hartley et al. ............ 260/553 A X |
| 3,925,446 | 12/1975 | Köppe et al. ............. 260/553 A X |
| 3,928,412 | 12/1975 | Smith ................... 260/553 R X |
| 3,930,016 | 12/1975 | Berntsson et al. ......... 424/300 |
| 3,935,259 | 1/1976 | Wilhelm ................. 260/553 A |
| 3,944,611 | 3/1976 | Smith ................... 260/553 A X |
| 3,959,369 | 5/1976 | Smith ................... 260/553 A X |
| 3,983,169 | 9/1976 | Zölss et al. ............. 260/553 A X |
| 3,998,790 | 12/1976 | Brandström et al. ....... 260/553 A X |

FOREIGN PATENTS OR APPLICATIONS

| | | |
|---|---|---|
| 292,671 | 9/1971 | Austria |
| 1,393,675 | 5/1975 | United Kingdom ......... 260/553 A |
| 1,396,322 | 6/1975 | United Kingdom ......... 260/553 A |
| 1,383,899 | 2/1975 | United Kingdom ......... 260/553 A |

OTHER PUBLICATIONS

Smith, CA 80:27003s (effective date 11/15/73).
Danilewicz et al., CA 74:99680j (1971).
Smith, CA 78:71716j (1973).
Wilhelm, CA 76:140273k (1972).

*Primary Examiner*—Daniel E. Wyman
*Assistant Examiner*—Thomas A. Waltz
*Attorney, Agent, or Firm*—Wenderoth, Lind & Ponack

[57] ABSTRACT

Phenoxypropylamine derivatives of the general formula:

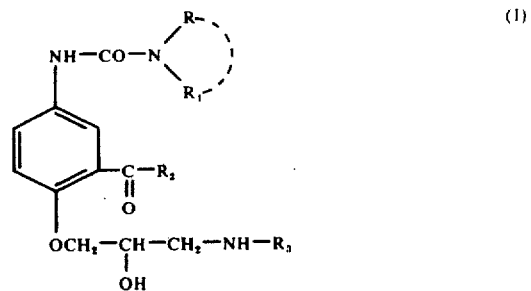

in which R is a hydrogen atom or a straight-chain or branched alkyl group containing up to 10 carbon atoms, $R_1$ is a hydrogen atom, a straight-chain or branched alkyl group containing up to 10 C atoms or a cyclopentyl, cyclohexyl, benzyl or phenyl group or R and $R_1$ taken together form a pentamethylene-(1,5), tetramethylene-(1,4), 2-azapentamethylene-(1,5), 3-azapentamethylene-(1,5) and 3-oxapentamethylene-(1,5)-group, $R_2$ is an alkyl group containing up to 6 carbon atoms or a benzyl or phenyl group and $R_3$ is a branched alkyl group containing 3 to 6 carbon atoms, a cyanoalkyl group containing up to 6 carbon atoms or a cycloalkyl group containing 3 to 7 carbon atoms, and pharmaceutically-acceptable salts thereof, having a cardio-selective β-blocking action.

7 Claims, No Drawings

4-UREIDO-2-ACYL PHENOXYPROPANOLAMINE

This invention relates to phenoxypropylamine derivatives and to a process for the preparation thereof. It is also concerned with pharmaceutical preparations containing these compounds.

Substances with a blocking action on the β-receptors are assuming increasing importance in therapy for the treatment of various cardiac illnesses which may be explained in terms of cause or symptoms by an undesirably high content of catecholamines, originating from the body, in the circulation. It has been possible to achieve a significant advance through the discovery of so-called cardio-selective β-blocking agents, that is to say agents which predominantly display an action only on the β-receptors of the heart but have little action on β-receptors of other organs, since in this way it is possible to aviod adverse side-effects such as, for example, a spastic effect on the respiratory tracts. However, of these selective agents hitherto only one compound, namely 1'-[4-acetamino-phenoxy(2'-hydroxy-3'-isopropylamino)]-propane, described in Austrian patent specification No. 261,582, has found acceptance in practice so that there continues to be a great need to find actually usable cardio-selective β-blocking agents. However, with many β-blocking agents an obstacle is an undesired cardiodepressive action which is frequently coupled with the β-blocking action.

The patent literature has also disclosed cardio-selective phenoxypropylamine derivatives, with a ureido group in the p-position relative to the propylamine side chain (DT-OS No. 2, 100,323) which may be substituted in the nucleus by hydrocarbon radicals, ether groups, halogen atoms, trifluoromethyl groups or nitrile groups, and also cardio-selective phenoxypropylamine derivatives with an alkanoylamide grouping in the p-position and acyl groups, for example the acetyl group, in the o-position relative to the propylamine side chain, see Austrian patent specification No. 292,671.

Surprisingly, it has now been found that phenoxypropylamine derivatives which carry a ureido group in the p-position to the phenoxypropylamine chain and an acyl group, preferably a lower alkanoyl group, in the o-position, and which have the general formula (I), as hereinafter defined, possess pronouncibly cardio-selective, β-blocking properties which are coupled with very good and reliable activity when administered perorally.

Accordingly, the present invention provides a phenoxypropylamine derivative of the general formula:

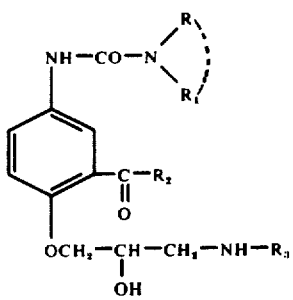

in which R is a hydrogen atom or a straight-chain or branched alkyl group containing up to 10 carbon atoms, $R_1$ is a hydrogen atom, a straight-chain or branched alkyl group containing up to 10 carbon atoms or a cyclopentyl, cyclohexyl, benzyl or phenyl group or R and $R_1$ taken together form a divalent, straight-chain or branched hydrocarbon group containing 4 to 7 carbon atoms in the main chain, it being possible for one or two of these carbon atoms to be replaced by oxygen, sulphur or nitrogen atoms, $R_2$ is an alkyl group containing up to 6 carbon atoms or a benzyl or phenyl group and $R_3$ is a branched alkyl group containing 3 to 6 carbon atoms, a cyanoalkyl group containing up to 6 carbon atoms or a cycloalkyl group containing 3 to 7 carbon atoms, and pharmaceutically-acceptable salts thereof.

The activity of the compounds of formula (I) may be determined on awake dogs by the method of Dunlop and Shanks, Brit. J. Pharmacol. 32, 201–18, 1968. The cardio-selective action may be recognised, for example, from the fact that according to the method of Shanks et al., Cardiologia Suppl. II, 49, 11 (1966), carried out on narcotised dogs, the increase in pulse rate occasioned by Isoprenalin is inhibited to a greater extent by prior administration of the above compounds than is the blood pressure lowering action of Isoprenalin. This action may also be seen in the case of rats from a blocking action on the Isoprenalin-conditioned increase in unesterified fatty acids ($β_1$-action) whilst hardly any effect on the lactate values and glucose values increased by Isoprenalin was found ($β_2$-action).

Surprisingly, in spite of the high β-blocking action, the compounds of the formula (I) cause no lowering of the pulse rate, after peroral administration of the substances, when testing the pulse rate on awake dogs by a method based on that of Barrett and Carter, Brit. J. Pharmacol. 40, 373–81 (1970); this indicated that the undesired and in part dangerous cardio-depressive action is absent in the case of the compounds of the formula (I). The toxicity of the compounds of the formula (I) in mice is the same as, or even lower than, that of the commercially available β-blocking agents.

The present invention also provides a process for the preparation of a compound of the formula (I), which comprises reacting a p-aminophenol derivative of the general formula:

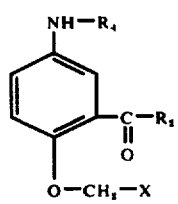

in which $R_4$ is a hydrogen atom or the

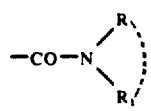

group, wherein R and $R_1$ are as defined above, and X is the

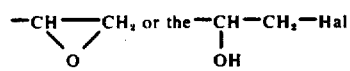

group, in which Hal is a chlorine, bromine or iodine atom, and $R_2$ is as defined above, or a mixture of compounds of the formula (II), in which X has both the definitions given, with an amine of the general formula:

$$H_2N - R_3 \quad (III)$$

in which $R_3$ is as defined in formula (I), at room temperature or elevated temperature, and, when $R_4$ in the resulting compound is a hydrogen atom, subsequently reacting the said resulting compound with a carbamic acid derivative of the formula:

in which $R_5$ is a halogen atom and $R_6$ has the meaning of R or $R_5$ and $R_6$ together represent a further bond between the carbon and nitrogen atoms, and R and $R_1$ are as defined above, so as to introduce the ureido group, and thereafter isolating the resulting compound of the formula (I) in the form of the free base or a salt thereof.

By elevated temperature there is to be understood a temperature between 30° C and 150° C, preferably a temperature below 120° C. In the case of compounds with ureido groups, which are substituted by two alkyl groups, it is advisable to carry out the reaction, if possible, at room temperature or only slightly above. The reaction may be carried out in a polar solvent, for example, in dimethylformamide, dioxane or tetrahydrofurane, but preferably in a lower aliphatic alcohol. It is also possible to use the amine of the formula (III) in such a large excess that it may, at the same time, serve as the solvent. Finally, however, it is also possible to conduct the process without a solvent, in which case the compound of the formula (III) may be present in a stoichiometric amount or in a slight excess. If the solvent or the amine of the formula (III) is volatile at the reaction temperature used, the reaction must be carried out in a closed system.

If X in the compound of the formula (II) is the

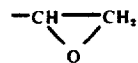

group, the reaction is particularly advantageously carried out at a temperature as low as room temperature, and the addition of water to the reaction mixture, in an amount ranging from a few percent to an amount at which it is still possible to achieve homogeneity of the reaction mixture during the reaction, markedly increases the reaction rate. Complete conversion may be achieved in a relatively short time.

Thus, for example, it is entirely possible to use an amount of added water corresponding to about 1:1 relative to the solvent, the amount of water depending in the main on the hydrophilic properties of the starting material and of the end products.

If X in the compound of the formula (II) is

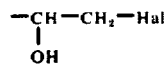

it is also possible to carry out the reaction with or without a solvent. In choosing the reaction conditions, the lower reactivity of the halohydrins as compared to the epoxy compounds of the formula (II) must be taken into account. As a rule, therefore, a higher temperature and a longer reaction time must be chosen. Temperatures within the range of 40° C to 120° C have proved advantageous. In this case, again, the addition of water, as described above, increases the reaction rate. In the case of this process it is again possible to work at room temperature except that longer reaction times, compared to the case of the epoxides, are required.

The compound of the formula (I) may be isolated from the reaction mixture in a customary manner. For example, the salts of the compounds of the formula I with dicarboxylic acids, for example the fumarates, oxalates, or succinates, have a very good tendency to crystallise and accordingly have advantages for isolation purposes. Of course, all customary pharmaceutically tolerated salts, for example the hydrohalides, such as hydrochlorides and hydrobromides, sulphates, phosphates, acetates, cyclohexyl-sulphamates, tartrates and citrates, also may be prepared.

The compounds of the formula I have an asymmetrical carbon atom. They therefore exist as the racemate and as optically active forms. The separation of the racemate into the optically active forms is achieved in the usual manner, for example by forming the diastereomeric salts with optically active acids, for example tartaric acid or camphorsulphonic acid.

The compounds of the formula (II) required as starting products are new in many cases. They may be obtained by reaction of the corresponding phenols with epihalohydrins. Epoxides of the formula (II) are obtained in the main when the phenolates are reacted with the epihalohydrin either in an anhydrous medium, for example in dimethylformamide or hexamethylphosphoric acid triamide as the solvent, or in water or an aqueous-alcoholic solution. The halohydrins are obtained if, after the reaction has taken place, excess epihalohydrin is distilled off and the residue is taken up in a suitable solvent, for example chloroform, and treated with aqueous hydrohalic acid. The halohydrins in most cases crystallise more easily than the epoxides so that their preparation is indicated in cases where, because of crystallisation difficulties, the epoxides cannot be obtained in a sufficiently pure form. The epoxides of the formula (II) obtained in the manner described above may contain proportions of halohydrin of the formula (II) which of course does not interfere with the further reaction to give the compounds of the formula (I).

The phenols with a previously formed side chain carrying the ureido group, which are required for the preparation of the compounds of the formula (II), also may be prepared in accordance with known methods. The starting materials for the preparation of compounds of the formula (II), in which R and $R_1$ are hydrogen atoms, may be obtained, for example, by reaction of the corresponding aniline salts with potassium cyanate. If it is desired to prepare compounds of the formula (II) in which R and/or $R_1$ are not hydrogen, the corresponding ureido-substituted phenol is obtained by reaction of the corresponding isocyanate, of which the phenolic hydroxyl group is protected by an acyl or benzyl group, with an amine of the formula $HNRR_1$, wherein R and $R_1$ are as defined above. The group which protects the phenolic hydroxyl group then may be split off easily. The ureido-substituted phenols also may be synthesised from carbamic acid chlorides.

Amongst the compounds of the formula (I), those compounds in which R is a hydrogen atom or a straight-chain or branched alkyl group containing up to 6, preferably up to 4, carbon atoms, display a particularly advantageous action.

For compounds with a particularly advantageous action, $R_1$ is a hydrogen atom, an optionally branched alkyl group containing up to 6, preferably up to 4, carbon atoms, a benzyl group or a phenyl group. Compounds in which R and $R_1$ together with the terminal nitrogen atom of the ureido group represent a pyrrolidino, diazolidino, for example imidazolidino, thiazolidino, oxazolidino, piperidino, porpholino, tetrahydrodiazino, for example tetrahydropyrimidino, tetrahydrothiazino or homopiperazino group also possess a favourable action. Compounds containing the pyrrolidino, piperidino or morpholino group are preferred in this respect.

Particularly favourable properties are exhibited, as a rule, by compounds in which each of R and $R_1$, which may be the same or different, is a hydrogen atom or an alkyl group containing 1 to 6, preferably 1 to 4, carbon atoms, or both groups together form a tetramethylene, pentamethylene or 3-oxapentamethylene group, $R_2$ is an alkyl group containing 1 to 5 carbon atoms and $R_3$ is a tertiary butyl group or isopropyl group.

The present invention further provides a pharmaceutical composition comprising, as the active ingredient, one or more compounds of formula (I) herein, in admixture with one or more pharmaceutically-acceptable excipients or diluents. The pharmaceutical compositions may be administered orally, rectally or parenterally, the nature of the excipient depending on the type of administration. The compositions may be in the form of tablets or dragees and the active compound, optionally together with a pharmaceutically acceptable solvent, may be made up into capsules.

Pharmaceutically tolerated soluble salts which are capable of forming stable solutions may be used in the form of injectable solutions. The salts required for this purpose are obtained in a simple manner from the corresponding bases of the formula (I) by reaction with the equivalent amount of acid. Both bases and salts may be converted to suppositories in the usual manner.

The individual dose for humans is preferably 100 mg. in the case of peroral administration and correspondingly lower in the case of intraveneous administration.

The following Examples illustrate the invention and the manner in which it may be performed:

EXAMPLE 1

172.3 g of N-[3-acetyl-4-(2',3'-epoxy)-propoxy]-phenyl-N'-diethyl-urea are mixed with 620 ml of water and 620 ml of tert. butylamine are added. The temperature of the reaction mixture rises to 40° C and the starting material rapidly dissolves. After a total of 5 hours at room temperature, the volatile constituents are distilled off on a rotary evaporator in vacuo at 40° C.

The residue is dissolved in 124 ml. of 4 N HCl and 500 ml of water and the acid solution is extracted with ethyl acetate, shaken with animal charcoal, filtered and mixed with 124 ml of 4 N NaOH. The base which separates out is extracted with ethyl acetate and the ethyl acetate solution is dried with $Na_2SO_4$, filtered and evaporated. The residue crystallises after digestion with ether. The crystals which separate out are filtered off and dried.

Yield: 167.4g = 78.4% of theory of N-[3-acetyl-4-(3'-tert.-butylamino-2'-hydroxy)-propoxy]-phenyl-N'-diethylurea.

Melting point of the base: 110° to 112° C.

EXAMPLE 2

A mixture of 8 ml of tert.-butylamine and 8 ml of water is added to 1.0 g. of N-[3-acetyl-4-(2'-hydroxy-3'-chloro)-propoxy]-phenyl-N'-diethylurea (melting point = 144° to 146° C) and the mixture is left to stand for 17 hours at room temperature. The clear reaction solution is evaporated in vacuo, the oily residue is dissolved in 1N HCl and the solution is extracted with ethyl acetate. The acid aqueous solution is rendered alkaline, the base which separates out is extracted with ethyl acetate and the organic layer is dried and evaporated. The oily residue crystallises after trituration with ether.

Yield of N-[3-acetyl-4-(3'-tert.-butylamino-2'-hydroxy)-propoxy]-phenyl-N'-diethylurea: 1.0 g = 90.4% of theory. Melting point: 110° to 112° C.

The following are obtained in an analogous manner to Examples 1 and 2:

EXAMPLE 3

N-[3-Acetyl-4-(3'-isopropylamino-2'-hydroxy)-propoxy]-phenyl-N'-diethylurea. Melting point of the base 107° to 109° C.

EXAMPLE 4

N-[3-Acetyl-4-(3'-tert.butylamino-2'-hydroxy)-propoxy]-phenyl-N'-dimethylurea. Melting point of the base: 121° to 122° C. Fumarate: melting point = 205° to 208° C obtained by adding the equivalent amount of fumaric acid in ethanolic solution to the solution of the base in acetone.

EXAMPLE 5:

N-[3-Acetyl-4-(3'-tert.-butylamino-2'-hydroxy)-propoxy]-phenylurea. Melting point of the hydrochlorid: 195° to 197° C.

EXAMPLE 6:

N-[3-Acetyl-4-(3'-tert.butylamino-2'-hydroxy)-propoxy]-phenyl-N'-methylurea. Melting point of the base: 132° to 134° C.

EXAMPLE 7

N-[3-Acetyl-4-(3'-tert.-butylamino-2'-hydroxy)-propoxy]-phenyl-N'-ethylurea. Melting point of the fumarate: 196° to 198° C.

EXAMPLE 8

N-[3-Acetyl-4-(3'-tert.-butylamino-2'-hydroxy)-propoxy]-phenyl-N'-isopropylurea. Melting point of the base: 87° to 90° C.

EXAMPLE 9

N-[3-Acetyl-4-(3'-tert.-butylamino-2'-hydroxy)-propoxy]-phenyl-N'-butylurea. Melting point of the base: 126° to 129° C.

EXAMPLE 10

N-[3-Acetyl-4-(3'-tert.-butylamino-2'-hydroxy)-propoxy]-phenyl-N'-sec.-butylurea. Melting point of the base: 80° to 82° C.

EXAMPLE 11

N-[3-Acetyl-4(3'-tert.-butylamino-2'-hydroxy)-propoxy]-phenyl-N'-tert.-butylurea. Melting point of the base: 123° to 125° C.

EXAMPLE 12

N-[3-Acetyl-4-(3'-ispropylamino-2'hydroxy)-propoxy]-phenyl-N'-dimethylurea. Melting point of the base: 103° to 107° C.

EXAMPLE 13

N-[3-Acetyl-4-(3'-cyclopropylamino-2'-hydroxy)-propoxy]-N'-dimethylurea. Melting point of the base: 80° to 83° C.

EXAMPLE 14

N-[3-Acetyl-4-(3'-tert.-butylamino-2'-hydroxy-propoxy]-phenyl-N'-methyl-N'-ethylurea. Melting point of the base: 90° to 93° C.

EXAMPLE 15

N-[3-Acetyl-4-(3'-tert.-butylamino-2'-hydroxy)-propoxy]-phenyl-N'-methyl-N'-butylurea. Melting point of the base: 84° to 86° C.

EXAMPLE 16

N-[3-Acetyl-4-(3'-tert.-butylamino-2'-hydroxy)-propoxy]-phenyl-N'-di-n-butylurea. The base crystallises in two modifications: Melting point (from ether): 81° to 83° C. Melting point (from methanol/water): 113° to 115° C.

EXAMPLE 17

N-[3-Acetyl-4-(3'-tert.-butylamino-2'-hydroxy)-propoxy]-phenyl-N'-di-n-propylurea. Melting point of the base: 83° to 86° C.

EXAMPLE 18

N-{3-Acetyl-4-[3'-(2''-cyano-propyl(2'')-amino)-2'-hydroxy]-propoxy}-phenyl-N'-diethylurea. Melting point of the base: 89° to 92° C.

EXAMPLE 19

N-[3-Acetyl-4-(3'-tert.butylamino-2'-hydroxy)-propoxy]-phenyl-N'-phenylurea. Melting point of the base: 159° to 164° C.

EXAMPLE 20

N-[3-Acetyl-4-(3'-tert.butylamino-2'-hydroxy)-propoxy]-phenyl-N'-tetramethylene (1,4)-urea. Melting point of the fumarate: 218° to 220° C.

EXAMPLE 21

N-[3-Acetyl-4-(3'-tert.-butylamino-2'-hydroxy)-propoxy]-phenyl-N'-pentamethylene(1,5)-urea. Melting point of the fumarate: 211° to 213° C.

EXAMPLE 22

N-[3-Propionyl-4-(3'-tert.-butylamino-2'-hydroxy)-propoxy]-phenylurea. Melting point of the fumarate: 204° to 207° C.

EXAMPLE 23

N-[3-Propionyl-4-(3'-tert.-butylamino-2'-hydroxy)-propoxy]-phenyl-N'-methylurea. Melting point of the fumarate: 134° to 136° C.

EXAMPLE 24

N-[3-Propionyl-4-(3'-tert.-butylamino-2'-hydroxy)-propoxy]-phenyl-N'-diethylurea. Melting point of the base: 107° to 109° C.

EXAMPLE 25

N-[3-Propionyl-4-(3'-tert.-butylamino-2'-hydroxy)-propoxy]-phenyl-N'-dimethylurea. Melting point of the fumarate: 199° to 202° C.

EXAMPLE 26

N-[3-Propionyl-4-(3'-tert.-butylamino-2'-hydroxy)-propoxy]-phenyl-N'-tetramethylene(1,4)-urea. Melting point of the fumarate: 208° to 211° C.

EXAMPLE 27

N-[3-Propionyl-4-(3'-tert.-butylamino-2'-hydroxy)-propoxy]-phenyl-N'-3-oxa-pentamethylene(1,5)-urea. Melting point of the fumarate: 193° to 195° C.

EXAMPLE 28

N-[3-Butyryl-4-(3'-tert.-butylamino-2'-hydroxy)-propoxy]-phenyl-N'-pentamethylene (1,5)-urea: Melting point of the fumarate: 167° to 170° C.

EXAMPLE 29

N-[3-Phenylacetyl-4-(3'-tert.-butylamino-2'-hydroxy)-propoxy]-phenyl-N'-pentamethylene(1,5)-urea. Melting point of the base: 117° to 118° C.

EXAMPLE 30

N-[3-Benzoyl-4-(3'-tert.-butylamino-2'-hydroxy)-propoxy]-phenyl-N'-pentamethylene(1,5)-urea. Melting point of the base: 120° and 123° C.

EXAMPLE 31

N-[3-Acetyl-4-(3'-tert.-butylamino-2'-hydroxy)-propoxy]-phenyl-N'-methyl-N'-isopropylurea. Melting point of the base: 105° to 107° C.

EXAMPLE 32

N-[3-Acetyl-4-(3'-tert.-butylamino-2'-hydroxy)-propoxy]-phenyl-N'-ethyl-N'-n-propylurea. Melting point of the fumarate: 176° to 178° C.

EXAMPLE 33

N-[3-Butyryl-4-(3'-tert.-butylamino-2'-hydroxy)-propoxy]-phenyl-N'-diethylurea. Melting point of the base: 56° to 58° C.

EXAMPLE 34

N-[3-Acetyl-4-(3'-tert.-butylamino-2'-hydroxy)-propoxy]-phenyl-N'-methyl-N'-benzylurea. Melting point of the base: 121° to 123° C.

EXAMPLE 35

N-[3-Acetyl-4-(3'-tert.-butylamino-2'-hydroxy)-propoxy]-phenyl-N'-methyl-N'-cyclohexylurea.

What we claim is:

1. A phenoxypropylamine derivative selected from the group consisting of compounds of the formula

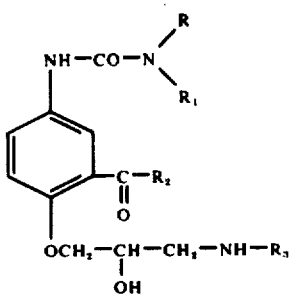

wherein R and $R_1$ which may be the same or different are an alkyl group containing 1 to 6 carbon atoms, $R_2$ is an alkyl group containing 1 to 5 carbon atoms and $R_3$ is tertiary butyl or isopropyl and pharmaceutically acceptable salts thereof.

2. A phenoxy propylamine compound according to claim 1 wherein $R_2$ is methyl and $R_3$ is tertiary butyl.

3. As compound, according to claim 1, N-[3-Acetyl-4-(3'-tert.-butylamino-2'-hydroxy)-propoxy]-phenyl-N'-diethylurea.

4. As compound according to claim 1, N-[3-Acetyl-4-(3'-tert.-butylamino-2'-hydroxy)-propoxy]-phenyl-N'-dimethylurea.

5. As compound according to claim 1, N-[3-Acetyl-4-(3'-tert.-butylamino-2'-hydroxy)-propoxy]-phenyl-N'-methyl-N'-ethylurea.

6. As compound according to claim 1, N-[3-Acetyl-4-(3'-tert.-butylamino-2'-hydroxy)-propoxy]-phenyl-N'-methyl-N'-n-butylurea.

7. As compound according to claim 1, N-[3-Butyryl-4-(3'-tert.-butylamino-2'-hydroxy)-propoxy]-phenyl-N'-diethylurea.

* * * * *